United States Patent
Yokota et al.

(10) Patent No.: US 7,034,188 B2
(45) Date of Patent: Apr. 25, 2006

(54) PRODUCTION METHOD OF KETONE COMPOUND

(75) Inventors: Tadafumi Yokota, Toda (JP); Hiroshi Yano, Osaka (JP)

(73) Assignee: Japan Energy Corporation, Tokyo (JP)

( * ) Notice: Subject to any disclaimer, the term of this patent is extended or adjusted under 35 U.S.C. 154(b) by 0 days.

(21) Appl. No.: 10/760,386

(22) Filed: Jan. 21, 2004

(65) Prior Publication Data

US 2004/0152922 A1    Aug. 5, 2004

(30) Foreign Application Priority Data

Jan. 24, 2003   (JP)   ............... P. 2003-015516

(51) Int. Cl.
*C07C 45/66*   (2006.01)

(52) U.S. Cl. ...................... 568/361; 568/375

(58) Field of Classification Search ............... 568/361, 568/375
See application file for complete search history.

(56) References Cited

U.S. PATENT DOCUMENTS 3,963,571 A * 6/1976 Bost ..................... 435/142

| 4,866,210 A | 9/1989 | Hoelderich et al. |
| 5,300,654 A * | 4/1994 | Nakajima et al. ............. 549/13 |

FOREIGN PATENT DOCUMENTS

| CH | 272 568 A | 12/1950 |
| GB | 762421 A | 11/1956 |
| JP | 3087921 B2 | 7/2000 |
| JP | 2002-220361 A | 8/2002 |

OTHER PUBLICATIONS

Patent Abstracts of Japan—2002 220361 A, vol. 2002, No. 12.
European Search Report dated Apr. 13, 2004.

* cited by examiner

*Primary Examiner*—Sikarl A. Witherspoon
(74) *Attorney, Agent, or Firm*—Sughrue Mion, PLLC

(57)   ABSTRACT

A method for producing a ketone, particularly a macrocyclic ketone, from a 2-hydroxycycloalkanone having from 12 to 18 carbon atoms by efficiently dehydrating and reducing the acyloin in a single reaction vessel. A method for producing a ketone compound, which comprises dehydrating and reducing an acyloin in the coexistence of an acid catalyst and a reduction catalyst and in the presence of hydrogen, particularly using a 2-hydroxycycloalkanone having from 12 to 18 carbon atoms as the acyloin.

6 Claims, No Drawings

PRODUCTION METHOD OF KETONE COMPOUND

FIELD OF THE INVENTION

This invention relates to a method for producing a ketone compound from an acyloin, particularly a method for producing a macrocyclic ketone compound having from 12 to 18 carbon atoms which is used as a technical product or an intermediate for aromatics and the like.

BACKGROUND OF THE INVENTION

When a fatty acid ester is allowed to react with metallic sodium in benzene, toluene or the like inert solvent, an acyloin ($\alpha$-hydroxy ketone) is obtained by so-called acyloin condensation. In this case, it is known that a medium to large ring acyloin is formed by intramolecular condensation when a diester of a fatty acid having 5 or more carbon atoms is used, and a method has been proposed for the production of cyclopentadecanone as one of musk aromatic components, by carrying out dehydration and reduction reactions using 2-hydroxycyclopentadecanone as this acyloin (Japanese Patent No. 3087921, JP-A-2002-220361).

Broadly known as this dehydration reduction reaction includes a method in which an acyloin is converted into corresponding ketone by directly reducing it in the presence of zinc and hydrochloric acid, sulfuric acid or the like mineral acid and a two-stage method in which an acyloin is firstly dehydrated to convert it into an $\alpha$, $\beta$-unsaturated ketone which is then hydrogenated to convert it into corresponding ketone. Regarding the former zinc-acid direct reduction method, it is considered that the reaction progresses through the transfer of two electrons from zinc to the carbonyl group of acyloin, subsequent leaving of the $\alpha$-position hydroxyl group and simultaneous addition of proton of the acid to the formed enolate, so that its reaction mechanism is completely different from the latter two-stage method in which the material is dehydrated and then reduced.

In the aforementioned zinc-acid direct reduction method, chemically equivalent amount of zinc is required and zinc is consumed simultaneously with the reaction, but a side reaction occurs in which zinc is wastefully consumed by simply reacting with the acid, so that it poses a problem in terms of a waste treatment such as recovery of zinc, and since the reduction reaction occurs on the metal surface, it is necessary to highly disperse zinc in the two phases of mineral acid aqueous solution and organic solvent, and for obtaining agitation necessary for the sufficient dispersion, it is necessary to use a reactor having a relatively small volume, so that it also poses a problem when scale up is taken into consideration for the improvement of production efficiency.

In the two-stage method, on the other hand, the dehydration reaction and hydrogenation reaction are carried out as separate steps, and the product is once separated after completion of the dehydration reaction and transferred into another reaction vessel to carry out the hydrogenation reaction, so that the reaction operations are complex and become a cause of increasing the cost.

Reference 1: Japanese Patent No. 3087921
Reference 2: JP-A-2002-220361

SUMMARY OF THE INVENTION

The invention solves the aforementioned problems, and the object of the invention is to provide a method for the production of a macrocyclic ketone from an acyloin, particularly a 2-hydroxycycloalkanone having from 12 to 18 carbon atoms, by efficiently dehydrating and reducing the acyloin in a single reaction vessel.

With the aim of solving the above problems, the present inventors have conducted intensive studies and, to our surprise, found as a result that when an acyloin is allowed to undergo the reaction in the coexistence of an acid catalyst and a reduction catalyst and in the presence of hydrogen, the dehydration and reduction reactions simultaneously progress, and the production yield also becomes high in comparison with the two-stage method in which the reduction reaction is separately carried out after the dehydration reaction, thus resulting in the accomplishment of the invention.

That is, the invention is a method for producing a ketone compound, which comprises dehydrating and reducing an acyloin in the coexistence of an acid catalyst such as of phosphoric acids or solid acids and a reduction catalyst and in the presence of hydrogen, particularly using a 2-hydroxycycloalkanone having from 12 to 18 carbon atoms as the aforementioned acyloin.

DETAILED DESCRIPTION OF THE INVENTION

Any acyloin can be used as the material of the invention without a difficulty, with the proviso that it is an acyloin ($\alpha$-hydroxy ketone) obtained by so-called acyloin condensation in which a fatty acid ester is allowed to react with metallic sodium in benzene, toluene or the like inert solvent.

Particularly, when 2-hydroxycycloalkanone, which is obtained by allowing a diester of a linear alkane dicarboxylic acid having from 12 to 18 carbon atoms to react with metallic sodium in benzene, toluene or the like inert solvent, is used as the material of the invention, a macrocyclic ketone useful as a musk aromatic component can be obtained.

According to the invention, an acyloin is dehydrated and reduced in the coexistence of an acid catalyst such as of phosphoric acids or solid acids and a reduction catalyst, and as the acid catalyst of this case, phosphoric acids such as orthophosphoric acid, metaphosphoric acid, pyrophosphoric acid and the like polyphosphoric acids, or solid acids such as silica alumina, zeolite or zirconia sulfate, zirconia alumina sulfate prepared by carrying sulfuric acid on zirconia and/or alumina (cf. JP-B-59-6181, JP-A-11-809727 and the like) or the like, can be used.

On the other hand, a nickel catalyst, a cobalt catalyst, a copper catalyst, a palladium catalyst, a platinum catalyst, a ruthenium catalyst, a rhodium catalyst and the like can be exemplified as the reduction catalyst.

Amount of these catalysts to be used varies depending on the kinds and active degrees of each catalyst, but in the case of the acid catalyst, it is desirable to optionally select it within the range of from 0.01 to 0.5 part by mass based on 1 part by mass of acyloin when the catalyst is one of phosphoric acids, or within the range of from 0.01 to 1 part by mass based on 1 part by mass of acyloin when the catalyst is one of the solid acids. Also, in the case of the reduction catalyst, it is desirable to optionally select it within the range of from 0.001 to 0.1 part by mass based on 1 part by mass of acyloin.

Though the reaction of the invention progresses without using a solvent, there is a case in the actual operation in which it is desirable to carry out the reaction in the form of a solution using a solvent. When a solvent is used, any solvent can be used without a difficulty with the proviso that it is inert to the reaction, but it is desirable from the viewpoint of convenience to use a saturated hydrocarbon or an aromatic hydrocarbon. When amount of the solvent to be used in this case is too large, the reaction becomes slow and an inconvenience such as worsening of the reaction efficiency per volume occurs, so that it is desirable to optionally select it within such a range that concentration of acyloin becomes 0.1 mole/liter or more.

It is desirable that the reaction temperature is controlled at a level of from 0 to 400° C., preferably from 150 to 300° C., and it is convenient to carry out the reaction in sealed hydrogen gas under the ordinary pressure, but it may be carried out by bubbling hydrogen gas or under a hydrogen pressure of from 0.01 to 5 MPa using an autoclave. In addition, it may also be carried out by a flow system in which the reaction solution and hydrogen gas are passed in parallel through packed catalysts.

The reaction time may be suitably selected within the range of 30 min. to 10 hrs. in consideration of the concentration of the acyloin or catalysts in the reaction solution, mixing rate and the like.

The thus obtained reaction product can be purified by distillation, chromatography and the like usual methods.

The ratios described in this specification by using a term "by mass" has the same meaning with the ratios with the use of "by weight".

The invention is described in the following with reference to illustrative examples, though the invention is not limited thereto.

INVENTIVE EXAMPLE 1

A 15.6 g portion of 2-hydroxycyclopentadecanone, 198 g of toluene, 3.5 g of a silica alumina catalyst (HA, mfd. by Catalysts & Chemicals Industries) and 0.44 g of 5% Pd/carbon (NX-Type, mfd. by N. E. Chemcat) were put into a 500 ml capacity autoclave and allowed to undergo the reaction at 250° C. by heating and stirring under a hydrogen pressure of 1 MPa. As an internal standard, decalin was added to the reaction solution 1 hour, 3 hours or 5 hours after commencement of the reaction, and the determination was carried out by a gas chromatography to calculate the yield of cyclopentadecanone based on 2-hydroxycyclopentadecanone. The results are shown in Table 1.

COMPARATIVE EXAMPLE 1

A 15.6 g portion of 2-hydroxycyclopentadecanone, 198 g of toluene and 3.5 g of a silica alumina catalyst (HA, mfd. by Catalysts & Chemicals Industries) were put into a 500 ml capacity autoclave and allowed to undergo the reaction at 250° C. by heating and stirring. As an internal standard, decalin was added to the reaction solution 1 hour, 3 hours or 5 hours after commencement of the reaction, and the determination was carried out by a gas chromatography to calculate the yield of cyclopentadecenone based on 2-hydroxycyclopentadecanone. The results are shown in Table 1.

TABLE 1

|  | One hour | Three hours | Five hours |
|---|---|---|---|
| Inventive Example 1 | 62% | 96% | 93% |
| Comparative Example 1 | 29% | 61% | 73% |

It can be understood from these results that the yield is evidently higher in Inventive Example 1 in which dehydration and reduction were directly carried out, even on the assumption that the cyclopentadecenone obtained in Comparative Example 1 could be converted into cyclopentadecanone at 100% efficiency.

REFERENCE EXAMPLE 1

A 15.6 g portion of 2-hydroxycyclopentadecanone, 198 g of toluene and 0.44 g of 5% Pd/carbon (NX-Type, mfd. by N. E. Chemcat) were put into a 500 ml capacity autoclave and allowed to undergo the reaction at 250° C. by heating and stirring under a hydrogen pressure of 1 MPa. As an internal standard, decalin was added to the reaction solution 1 hour, 3 hours or 5 hours after commencement of the reaction, and the determination was carried out by a gas chromatography to calculate the conversion ratio of 2-hydroxycyclopentadecanone. The results are shown in Table 2.

REFERENCE EXAMPLE 2

A 15.4 g portion of cyclopentadecanone, 185 g of toluene and 3.5 g of a silica alumina catalyst (HA, mfd. by Catalysts & Chemicals Industries) were put into a 500 ml capacity autoclave and allowed to undergo the reaction at 250° C. by heating and stirring under a hydrogen pressure of 1 MPa. As an internal standard, decalin was added to the reaction solution 1 hour, 3 hours or 5 hours after commencement of the reaction, and the determination was carried out by a gas chromatography to calculate the remaining ratio of cyclopentadecanone. The results are shown in Table 2.

TABLE 2

|  | One hour | Three hours | Five hours |
|---|---|---|---|
| Reference Example 1 | 0% | 0% | 0% |
| Reference Example 2 | 89% | 76% | 71% |

Since acyloin does not react under reduction reaction condition as can be seen from the results of Reference Example 1, it can be understood that the dehydration reaction and reduction reaction simultaneously progress in the same vessel by the method of the invention. In addition, the results of Reference Example 2 show that the ketone of interest changes to other compound when it is treated under the dehydration condition for a prolonged period of time. However, it can be understood that such a change hardly occurs when treated under both conditions of dehydration and reduction reactions like the case of the method of the invention.

Since the invention can carry out dehydration reaction and reduction reaction simultaneously in one reaction vessel with good yield, it exerts particular effect of being able to produce a ketone by efficiently dehydrating and reducing an acyloin.

While the invention has been described in detail and with reference to specific embodiments thereof, it will be apparent to one skilled in the art that various changes and modifications can be made therein without departing from the scope thereof.

This application is based on Japanese patent application No. 2003-015516 filed Jan. 24, 2003, the entire contents thereof being hereby incorporated by reference.

What is claimed is:

1. A method for producing a ketone compound, which comprises simultaneously dehydrating and hydrogenating an acyloin in the coexistence of an acid catalyst and a hydrogenation catalyst and in the presence of hydrogen.

2. The method for producing a ketone compound according to claim 1, wherein the acid catalyst is phosphoric acids or solid acids.

3. The method for producing a ketone compound according to claim 1, wherein the acyloin is a 2-hydroxycycloalkanone having from 12 to 18 carbon atoms.

4. The method for producing a ketone compound according to claim 1, wherein the hydrogenation catalyst is at least one member selected from the group consisting of a nickel catalyst, a cobalt catalyst, a copper catalyst, a palladium catalyst, a platinum catalyst, a ruthenium catalyst, and a rhodium catalyst.

5. A method for producing a ketone compound, which comprises simultaneously dehydrating and reducing an acyloin in the coexistence of an acid catalyst and a reduction catalyst and in the presence of hydrogen;

wherein the acid catalyst is phosphoric acids or solid acids; and wherein the reduction catalyst is at least one member selected from the group consisting of a nickel catalyst, a cobalt catalyst, a copper catalyst, a palladium catalyst, a platinum catalyst, a ruthenium catalyst, and a rhodium catalyst.

6. The method for producing a ketone compound according to claim 5, wherein the acyloin is a 2-hydroxycycloalkanone having from 12 to 18 carbon atoms.

* * * * *